US011554087B2

(12) United States Patent
Bradford et al.

(10) Patent No.: US 11,554,087 B2
(45) Date of Patent: Jan. 17, 2023

(54) SHAVING AID COMPRISING AN ANTIOXIDANT

(71) Applicant: The Gillette Company LLC, Boston, MA (US)

(72) Inventors: Valerie Jean Bradford, Framingham, MA (US); Erte Xi, Mason, OH (US); Alison Fiona Stephens, Maidenhead (GB); Ilaria Ambrogio, London (GB)

(73) Assignee: The Gillette Company LLC, Boston, MA (US)

(*) Notice: Subject to any disclaimer, the term of this patent is extended or adjusted under 35 U.S.C. 154(b) by 189 days.

(21) Appl. No.: 17/089,867

(22) Filed: Nov. 5, 2020

(65) Prior Publication Data
US 2022/0133611 A1    May 5, 2022

(51) Int. Cl.
A61Q 5/00     (2006.01)
A61K 8/37     (2006.01)
A61K 8/362    (2006.01)
A61K 8/81     (2006.01)
A61K 8/86     (2006.01)
A61Q 9/02     (2006.01)

(52) U.S. Cl.
CPC ............... A61K 8/37 (2013.01); A61K 8/362 (2013.01); A61K 8/8129 (2013.01); A61K 8/86 (2013.01); A61Q 9/02 (2013.01)

(58) Field of Classification Search
CPC ... A61Q 9/02; A61K 8/86; A61K 8/37; A61K 8/362
USPC ........................................................ 424/70.1
See application file for complete search history.

(56) References Cited

U.S. PATENT DOCUMENTS

| 5,349,750 | A | | 9/1994 | Tseng |
| 5,431,906 | A | * | 7/1995 | Mohseni .................. A61K 8/86 424/DIG. 5 |
| 5,922,331 | A | | 7/1999 | Mausner |
| 6,161,288 | A | | 12/2000 | Andrews |
| 6,298,558 | B1 | | 10/2001 | Tseng et al. |
| 6,301,785 | B1 | | 10/2001 | Kwiecien et al. |
| 6,442,839 | B1 | | 9/2002 | Tseng et al. |
| 6,449,849 | B1 | | 9/2002 | Hackerman |
| 7,024,776 | B2 | | 4/2006 | Wain |
| 7,168,173 | B2 | | 1/2007 | Worrick, III |
| 7,197,825 | B2 | | 4/2007 | Walker et al. |

(Continued)

FOREIGN PATENT DOCUMENTS

BR   102012029690 A2   9/2014
CN      108401417 A    8/2018

(Continued)

OTHER PUBLICATIONS

STIC Search Report dated Jun. 30, 2022.*

(Continued)

Primary Examiner — Eisa B Elhilo
(74) Attorney, Agent, or Firm — Kevin C. Johnson

(57) ABSTRACT

A shaving aid including a lubricant and an antioxidant in accordance with general formula (I). Also provided is shaving aid including a lubricant and an antioxidant in accordance with general formula (I), in which the lubricant includes a water soluble polymer with an initial molecular weight of at least 1,000,000 g/mol. The water soluble polymer exhibits a molecular weight loss of less than 500,000 g/mol within a predefined time period.

19 Claims, 4 Drawing Sheets

(56) References Cited

U.S. PATENT DOCUMENTS

| | | | |
|---|---|---|---|
| 7,607,230 | B2 | 10/2009 | Aviza et al. |
| 8,404,257 | B1* | 3/2013 | Huglin .................. C11D 3/0084 424/59 |
| 9,006,292 | B2 | 4/2015 | Raghavan |
| 10,080,763 | B2 | 9/2018 | Bhalani et al. |
| 10,682,778 | B2 | 6/2020 | Hayes et al. |
| 2005/0066526 | A1 | 3/2005 | Guimont |
| 2008/0034590 | A1 | 2/2008 | Prudden, Jr. et al. |
| 2008/0060201 | A1 | 3/2008 | Kwiecien |
| 2009/0004695 | A1 | 1/2009 | Szabo et al. |
| 2009/0092561 | A1* | 4/2009 | Lupia .................... A61Q 19/02 424/59 |
| 2011/0041865 | A1 | 2/2011 | Stephens et al. |
| 2012/0023763 | A1 | 2/2012 | Ariyanayagam et al. |
| 2015/0283715 | A1* | 10/2015 | Stephens .............. C10M 107/34 30/41 |
| 2017/0002288 | A1 | 1/2017 | Bradford et al. |
| 2017/0334082 | A1 | 11/2017 | Hayes et al. |
| 2018/0117780 | A1 | 5/2018 | Moloney et al. |
| 2021/0322290 | A1* | 10/2021 | Lynch .................... A61K 8/73 |

FOREIGN PATENT DOCUMENTS

| | | |
|---|---|---|
| EP | 2101719 B1 | 9/2009 |
| KR | 20170075364 A | 7/2017 |
| KR | 20170114539 A | 10/2017 |
| KR | 101800859 B1 | 11/2017 |
| KR | 1815225 B1 | 1/2018 |
| KR | 20180017459 A | 2/2018 |
| WO | 0025731 A1 | 5/2000 |
| WO | 2009092561 A1 | 7/2009 |
| WO | 2014182904 A2 | 11/2014 |
| WO | 2017003899 A1 | 1/2017 |
| WO | 2020047241 A1 | 3/2020 |
| WO | 2021207436 A1 | 10/2021 |

OTHER PUBLICATIONS

15921 PCT Search Report and Written Opinion for PCT/US2021/057681 dated Feb. 18, 2022, 7 Pages.

Mintel Razor, Procter & Gamble, URL Link; http://www.gnpd.com; dated Oct. 2021, 3 pages.

Mintel Rosegold Metal Handle Razor, Procter & Gamble, URL Link; http://www.gnpd.com; dated Oct. 2021, 3 pages.

* cited by examiner

SHAVING AID COMPRISING AN ANTIOXIDANT

FIELD

The present disclosure is directed to a shaving aid comprising a lubricant and an antioxidant.

BACKGROUND

Hair removal devices such as razors and hair removal heads such as razor cartridges often incorporate shaving aids to provide lubrication benefits during use. Shaving aids may include a lubricant and a carrier matrix such as a structurant or polymer matrix in which the lubricant is dispersed. Alternately, the lubricant may comprise a major portion of the shaving aid and the shaving aid may lack a carrier matrix, such as in pressed-pellet type shaving aids, or shaving aids included in a container. Shaving aids that include a polymer matrix may include extruded shaving aids in which the carrier matrix material is a polymer. Shaving aids that include a structurant may include melt-formed shaving aids in which the carrier matrix material is a non-polymeric room-temperature solid.

Shaving aids can also take a variety of forms. One common form is the lubristrip, which is typically integrated into the hair removal head such as the cartridge of a razor to provide lubrication during shaving. Another common form is a "wing" or "soap wing" which are disposed outward of the cartridge, and generally attached to it. Other common forms include pressed powders such as tablets and liquid shaving aids that may be used separately from the hair removal device or dispensed from a container within the hair removal device.

The lubricant is most commonly composed, at least partly, of polyethylene oxide (PEO), also called POLYOX™ (Dow Chemical). PEO is a high molecular weight water soluble polymer. When activated by water during the shave cycle, the PEO deposits onto the skin, adding a layer of lubrication. PEO in water is a viscoelastic fluid, and the rheological properties are directly correlated to the coefficient of friction (CoF) of the fluid. As the molecular weight of the polymer increases, the viscoelastic fluid properties increase as well, which can lead to a lower CoF.

Many currently marketed shaving aids use a matrix polymer material of high impact polystyrene (HIPS). The shaving aid is formed by co-extruding the matrix polymer (e.g. HIPS) and the PEO under set conditions. Importantly, the matrix (i.e., the HIPS) must be flowable during extrusion, which requires heating and/or shearing of the HIPS/PEO mixture.

High temperatures and/or shear such as that experienced during processing, or storage and use conditions such as high temperatures and/or exposure to water and/or oxygen, can limit the stability (i.e., in-process stability and long-term stability such as on-shelf stability) of the PEO. Further, the availability and/or effectiveness of stabilizing agents may be limited by the processing conditions (i.e. temperature, shear). By way of example, commercially available PEO products may include an antioxidant, such as butylated hydroxytoluene (BHT), to help maintain the stability of the PEO. Unfortunately, BHT and other known antioxidants suffer from one or more critical disadvantages when applied to shaving aids, and particularly to shaving aids that are heated and/or sheared during manufacture.

Thus, there is a need for an improved shaving aid that maintains the stability of the lubricant and avoids the known disadvantages of antioxidants.

SUMMARY OF THE INVENTION

The present disclosure provides a shaving aid, suitable for use with a hair removal device, comprising a lubricant and an antioxidant. The shaving aid may further comprise a chelant which may be selected from a group consisting of citric acid and ethylenediaminetetraacetic acid. The shaving aid of the present disclosure may further comprise a matrix polymer, such as ethylene vinyl acetate. The shaving aid may further comprise a non-polymeric matrix.

In another aspect of the disclosure, the lubricant includes a water soluble polymer that has an initial molecular weight of at least 1,000,000 g/mol and exhibits a molecular weight loss of less than about 500,000 g/mol within a predefined time period.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION

The present disclosure relates to a shaving aid suitable for use with a hair removal device, in which the shaving aid possesses desirable properties that improve the shave experience. Without wishing to be bound by theory, it is believed that the shaving aid compositions of the present disclosure help to preserve the stability (e.g. molecular weight) of the lubricant portion of the shaving aid to provide for an enhanced shaving experience.

Hair Removal Device

According to some examples of the disclosure, the shaving aid finds particular application for hair removal devices. Hair removal devices generally comprise a hair removal head and a handle or grip portion, upon which the hair removal head is mounted, either permanently or detachably/attachably. The hair removal device can be manual or power driven and can be used for wet and/or dry application. In some examples, the hair removal head may include a wide scraping surface, such as where the hair removal device is used with a depilatory, or a foil where the device is a shaving razor. In other examples, with reference to FIG. 1, the hair removal head may be a razor cartridge 10.

The hair removal head may be pivotally connected to a connecting structure that in turn, or independently (e.g. permanently fixed), is connected to a handle. In some examples, the connecting structure includes at least one arm to releasably engage the hair removal head. The hair removal head may be integral with the handle so that the hair removal device is discarded as a whole unit, or may comprise a detachable hair removal head that forms part of a shaving system, in which the detachable hair removal head is uncoupled from the handle and disposed of and a new detachable hair removal head is coupled to the same handle.

Figure 1:
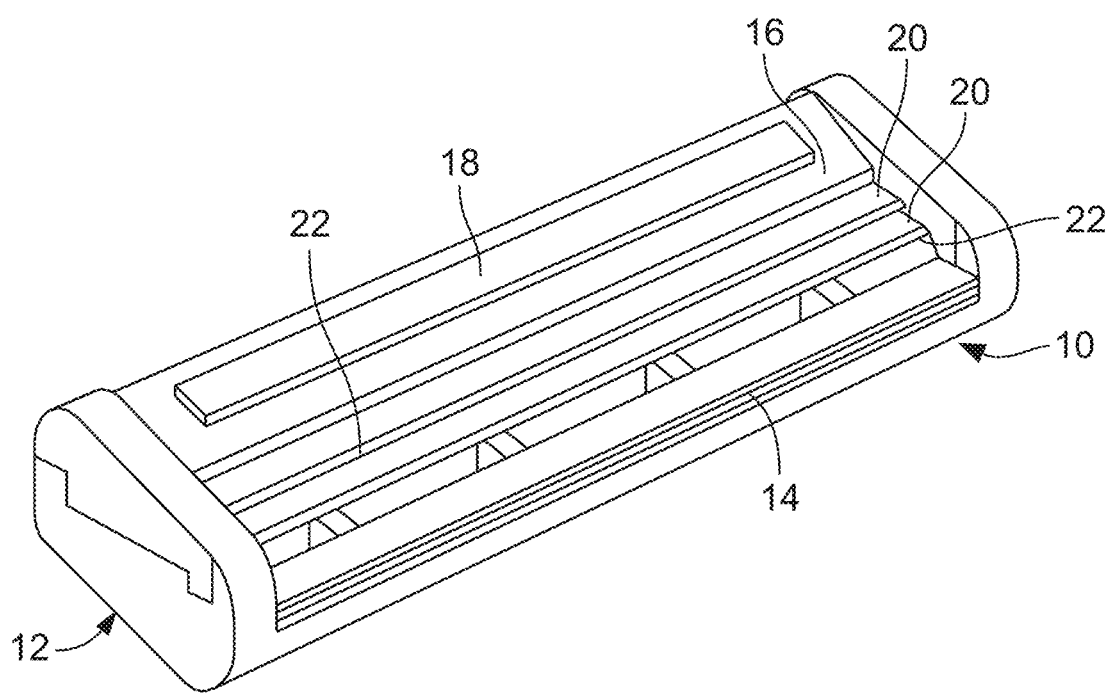
FIG. 1 is a perspective view of a razor cartridge comprising a shaving aid in accordance with the present disclosure.

The hair removal head typically comprises one or more elongated edges usually positioned between a first and second end, the one or more elongated edges comprising a tip extending forwardly. With reference to FIG. 1, where the hair removal head is a razor cartridge 10, the cartridge 10 may comprise a housing 12, and the one or more elongated edges can include one or more razor blades 20 incorporated into the housing 12, in which each blade 20 includes a blade edge 22.

A variety of razor cartridges can be used in accordance with the present disclosure. For example, U.S. Pat. No. 7,168,173 generally describes a FUSION® razor that is commercially available from The Gillette Company and which includes a razor cartridge with multiple blades. Non limiting examples of suitable razor cartridges, with and without fins, guards, and/or shave aids, include those marketed by The Gillette Company under the FUSION®, VENUS® product lines (Gillette) as well as those disclosed in U.S. Pat. Nos. 7,197,825, 6,449,849, 6,442,839, 6,301,785, 6,298,558, 6,161,288, and U.S. Patent Application Publication No. 2008/060201. Those of skill in the art will understand that the shaving aid can be used with any currently marketed razor or shaving system, including those having 2, 3, 4 or more blades. In such a case, the hair removal device is a razor, the hair removal head is a razor cartridge, and the one or more elongated edges are blades. Another example of a hair removal device is a scraping tool for use with a hair removal composition, i.e., a depilatory.

In some examples, at least one shaving aid is located on a portion of the cartridge that contacts skin during the hair removal process, forward and/or aft of the blades 20. A feature "forward" of the one or more elongated edges, for example, is positioned so that the surface to be treated by the hair removal device encounters the feature before it encounters the elongated edges. A feature "aft" of the elongated edge is positioned so that the surface to be treated by the hair removal device encounters the feature after it encounters the elongated edges.

In the example shown in FIG. 1, a shaving aid 18 is positioned on a cap 16 of the razor cartridge 10. In other examples, a plurality of shaving aids may be provided on the hair removal head, in which the plurality of shaving aids may be the same (identical) or different in terms of physical shape/structure and/or chemical composition. These shaving aids may be placed collectively (for example adjacent to one another) ahead of or behind the elongated edges (e.g. blades on a razor cartridge), including side by side, or separately with one ahead of the elongated edges and the other behind.

The shaving aid may be separate from or attached to the hair removal device or head. The shaving aid may be attached to the hair removal device or head by any suitable attachment means such as adhesive or interference fit or may be contained at least partially within a container. Exemplary embodiments of shaving aids contained in containers include US2011/0041865 and US2012/0023763. The shaving aid may be formed in the container by any means. The shaving aid may be compressed directly in the container.

In some examples, as shown in FIG. 1, the cartridge 10 comprises a guard 14 comprising at least one elongated flexible protrusion (not labeled) to engage a user's skin. The at least one flexible protrusion may comprise flexible fins generally parallel to the one or more elongated edges. The at least one flexible protrusion may additionally or alternatively comprise flexible fins comprising at least one portion which is not generally parallel to the one or more elongated edges. Non-limiting examples of suitable guards include those used in current razor blades and include those disclosed in U.S. Pat. Nos. 7,607,230 and 7,024,776; (disclosing elastomeric/flexible fin bars); and U.S. Patent Application Publication Nos. 2008/0034590 (disclosing curved guard fins) and 2009/0049695A1 (disclosing an elastomeric guard having guard forming at least one passage extending between an upper surface and a lower surface). In some examples, the shaving aid is positioned on the cartridge aft of the guard and forward of the elongated edge. In another example, the shaving aid is positioned on the cartridge forward of the guard. This example can be particularly useful to deliver the shaving aid prior to contact with the guard.

Water Soluble Polymer

The shaving aid may comprise a lubricant comprising a water soluble polymer, which provides lubrication during the shave once the water soluble polymer forms at least a partial solution with water. Examples of suitable water soluble polymers may include polyethylene oxide (PEO), polyvinyl pyrrolidone, polyacrylamide, polyhydroxymethacrylate, polyvinyl imidazoline, polyethylene glycol (PEG), polyvinyl alcohol, polyhydroxyethymethacrylate, copolymers of PEO and polypropylene oxide (PPO), guars, celluloses, modified celluloses, and mixtures thereof. Preferably, the water soluble polymer is PEO, and in some examples, the water soluble polymer may be selected from high and/or low molecular weight PEO referred to in the industry as PEO and PEG respectively.

According to the present disclosure, the shaving aid may comprise a lubricant comprising from about 1% to about 99% by weight of the shaving aid, preferably at least about 15%, more preferably at least about 20%, most preferably at least about 25%, and up to about 70%, preferably up to about 60% by weight of the shaving aid. The lubricating material preferably comprises at least 50% PEO by weight of the lubricant.

The water soluble polymer (especially PEO) may have a number-average molecular weight of at least about 20,000 g/mol, preferably at least about 50,000, more preferably at least about 100,000 or from about 100,000 to about 10 million, or about 300,000 to about 8 million, or from about 1 million to about 5 million or about 2 million to about 3 million. The PEO may have a number-average molecular weight of about 5 million (all values are ±10,000 g/mol).

The PEO may include a blend of different PEOs of differing molecular weights so that the weighted-average of the component PEO's fall within the desired molecular weight range for the PEO. The PEO blend may comprise about 40% to 80% of PEO having an average molecular weight of about 5 million (e.g. POLYOX™ Coagulant; Dow Chemical) and about 60% to 10% of PEO having an average molecular weight of about 300,000 (e.g. POLYOX™ WSR-N-750; Dow Chemical). The PEO blend may comprise about 40% to 80% of PEO having an average molecular weight of about 8 million (e.g. POLYOX' 308) and about 60% to 10% of PEO having an average molecular weight of about 300,000 (e.g. POLYOX™ WSR-N-750; Dow Chemical). The PEO blend may also advantageously contain up to about 10% (for example about 5%) by weight of a low molecular weight (i.e. MW<10,000) PEG such as PEG-100.

Suitable copolymers of PEO and PPO may have an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the shaving aid in aqueous conditions, especially in combination with a further water soluble polymer (particularly PEO), and thus prevent an undesirable feeling in use.

The PEO/PPO copolymer may advantageously be a block copolymer, preferably a tri-block copolymer having the sequence: PEO-PPO-PEO, the latter being commercially available under tradenames such as PLURACARE® (BASF) and PLURONIC® (BASF).

The PEO/PPO copolymer may have a weight ratio of PEO to PPO, of from 1000:1 to 1:1000 or from 100:1 to 1:100. The PEO/PPO copolymer is typically present at an amount of from 0.01% to 50%, preferably from 0.01% to 50%, more preferably from 2% to 40%, even more preferably from 3% to 25%, even more preferably still from 4% to 20% and most preferably from 5% to 10% by weight of the lubricating material or by weight of the shaving aid.

The shaving aid and/or water soluble polymer preferably comprises less than 5%, preferably less than 1% by weight and more preferably is/are substantially free of lathering soaps (i.e. salts of fatty $C_4$ to $C_{30}$ acids) and lathering surfactants. A lathering surfactant is defined as a surfactant which when combined with water and mechanically agitated, generates a foam or lather. Lathering surfactants may include anionic and amphoteric lathering surfactants and mixtures thereof. Anionic lathering surfactants may include sarcosinates, sulfates, sulfonate, isethionate, taurates, phosphates, lactylates, glutamates, alkali metal salts of fatty acids (i.e. soaps) having from 8 to 24 carbons, and mixtures thereof.

Antioxidant

The shaving aid further comprises one or more antioxidants. Antioxidants act as stabilizing agents and may improve the in-process stability and/or extend the shelf life of the shaving aid by, for example, helping to maintain the stability of the water soluble polymer, e.g., by preventing loss of molecular weight. The antioxidant may be present in an amount of from about 0.1% to about 5% by weight of the shaving aid, preferably about 0.1% to about 3%, and more preferably about 1.5% (all values are ±0.01%). Without intending to be bound by theory, it is believed that including antioxidant at a level above 5% may impact the performance of the shaving aid due, at least in part, to the need to reduce the amount of lubricant to accommodate the increased level of antioxidant.

In accordance with the present disclosure, the antioxidant comprises one or more sterically hindered phenolic antioxidants, preferably a sterically hindered phenol of the general formula:

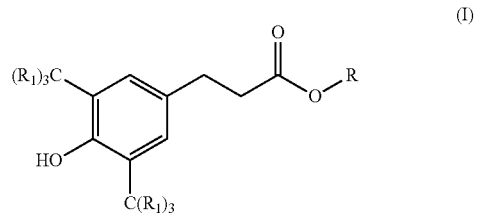

In Formula (I):

R may be a $C_{1-18}$ alkyl, a $C_{6-18}$ aryl, or a $C_{1-18}$ alkylaryl group; and $R_1$ may be a methyl group or a hydrogen atom or combination thereof.

In some examples, R may preferably be $<C_{12}$, more preferably $<C_6$, and even more preferably $<C_2$. In some particular examples, R may be $C_1$ (methyl) or $C_2$ (ethyl). The antioxidant may preferably be methyl 3,5-bis(1,1-dimethylethyl)-4-hydroxy-benzylpropionate (sold under the tradename RALOX™ 35 from Raschig GmbH; also referred to herein as Ralox 35), which has the formula:

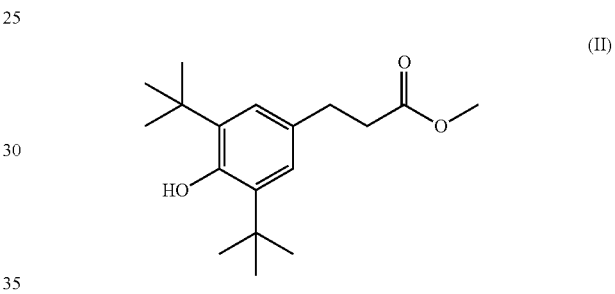

As discussed in more detail below with respect to the Examples, testing found that shaving aid formulations comprising certain antioxidants experienced an unacceptable amount of degradation over time, specifically reduction of the molecular weight of the water soluble polymer. Surprisingly, antioxidants such as TINOGARD® TS (BASF) and butylated hydroxytoluene (BHT) that share similarities in chemical structure with RALOX™ 35 and/or comprise a similar molecular weight, exhibited much higher reductions in molecular weight, as compared to the inventive examples comprising RALOX™ 35. In addition, while some formulations retained an acceptable molecular weight during testing, other unsatisfactory results were observed that would render them unacceptable for use in a shaving aid. For example, formulations comprising propyl gallate (PG) discolored over time showing the appearance of black specks which may have been due to complexation of the PG with iron ions (e.g. from tap water). Formulations comprising IONOL™ 220 (Oxiris) became discolored (e.g., turning yellow) during testing.

Chelant

The shaving aid may further comprise one or more chelants. The chelant may comprise from about 0.1% to about 5% by weight of the shaving aid, preferably about 0.1% to about 3%, more preferably about 0.1% to about 1.0%, and even more preferably about 0.5% (all values are ±0.01%). Without intending to be bound by theory, it is believed that including higher levels of chelant, i.e., above 5%, may impact production of the shaving aid. Specifically, it has been observed that higher chelant levels can create difficulties in the extrusion process. While higher chelant levels may be acceptable for a pressing production method, it may generally be preferred to include a chelant level at or below 5% by weight of the shaving aid for reasons similar to those discussed above with respect to the antioxidant.

Multiple chelants are known in the art. In some examples, the chelant may be ethylenediaminetetraacetic acid (EDTA), and in some preferred examples, the chelant may be citric acid. Surprisingly, testing found that shaving aids comprising the commonly-used chelant EDTA performed less favorably than shaving aids comprising Citric Acid. Furthermore, a specific chelant may be chosen based on the processing temperature and technique used to manufacture the shaving aid. If an incompatible combination of processing temperature/technique and chelant is chosen, the chelant may decompose during manufacture. For example, Citric Acid is not compatible with the process temperatures of high impact polystyrene (HIPS)-based shaving aids, as the Citric Acid decomposes at the 185° C. process temperature.

Carrier Matrix

The shaving aid may comprise a carrier matrix (also referred to herein as a "carrier") that provides structural integrity to the shaving aid and may enhance the life of the lubricant by reducing its tendency to be mechanically eroded. Advantageously, the carrier may be solid at standard temperature and pressure. The lubricant may comprise from about 1% to about 50%, preferably from about 10% to about 40%, and more preferably from about 20% to about 40%, by weight of the carrier. In some examples, the carrier material may fall under the definition of hydrophobic compound as used herein, and in such a case, should be included for purposes of determining the amount by weight of the hydrophobic compound or mixture.

In some examples, the carrier may comprise a matrix polymer such as ethylene vinyl acetate (EVA). Examples of shaving aids comprising EVA may be found in, for example, U.S. Pat. No. 5,349,750 and 10,682,778. In other examples, the carrier may comprise a polymeric matrix material such as HIPS. Further examples of a matrix polymer may include ethyl cellulose; polycaprolactone (PCL); polyethylene, polypropylene; polystyrene; butadiene-styrene copolymer (e.g. medium impact polystyrene and HIPS); polyacetal; acrylonitrile butadiene-styrene (ABS) copolymer; and blends such as polypropylene/polystyrene blend, and mixtures thereof.

Shaving aids comprising HIPS are typically formed by extruding a mixture that is heated to approximately 200° C. and exposed to shear during extrusion. These high processing temperatures and high shear conditions may limit the stability of the lubricant and/or the viability of compatible stabilizing agents. As such, the use of a lower temperature processable polymer matrix material such as EVA, which requires a lower processing temperature of approximately 130° C., or a melt-formed composition may be preferable.

Melt-formed shaving aids may include a non-polymeric matrix or structurant as part of the carrier, in which the non-polymeric structurant has a melt temperature of less than 100° C. In some examples, the non-polymeric structurant may comprise a lipophilic structurant. Suitable lipophilic structurants for use herein include $C_{14}$ or greater, preferably $C_{14}$ to $C_{22}$, more preferably $C_{16}$ to $C_{18}$, chain length fatty acyls such as fatty acids, fatty alcohols and esters, triglycerides, waxes, and mixtures thereof. Particularly preferred are $C_{14}$-$C_{22}$ alcohols, in particular cetyl, stearyl, and behenyl alcohols and mixtures thereof.

Suitable lipophilic structurants also include natural, synthetic, and silicone waxes. As used herein, the term "wax" includes, but is not limited to, any material that is solid at 45° C., preferably at 25° C.; and are very slightly soluble in water, preferably practically insoluble in water according to the United States' Pharmacopeia (USP) definition in 31/NF 26 Vol. 2 General Notices, Page Xvii. According to that definition, this means that 1000 to 10000 parts of water are needed to dissolve 1 part solute and that more than 10,000 parts of water are needed to dissolve 1 part solute respectively.

The lipophilic structurant and/or shaving aid preferably comprises less than 5%, preferably less than 1% by weight and more preferably is substantially free of lathering soap (i.e. salts of fatty acids such as $C_4$-$C_{30}$ carboxylic acids) or lathering surfactant. A lathering surfactant is defined as a surfactant which when combined with water and mechanically agitated generate a foam or lather. Lathering surfactants include anionic and amphoteric lathering surfactants and mixtures thereof. Anionic lathering surfactants include sarcosinates, sulfates, sulfonate, isethionate, taurates, phosphates, lactylates, glutamates, alkali metal salts of fatty acids (i.e. soaps) having from 8 to 24 carbons, and mixtures thereof.

The wax may comprise natural wax, synthetic wax or mixtures thereof. Natural waxes may be plant, animal or mineral derived. Non-limiting examples of suitable natural waxes include Beeswax, *Copernicia cerifera* (Carnauba) Wax, *Euphorbia cerifera* (Candelilla) Wax, Jojoba Wax, *Oryza Sativa* (Rice) Bran Wax, Lemon peel wax, Soybean wax, Sunflower wax and mixtures thereof.

Non-limiting examples of suitable synthetic waxes include Hydrogenated Jojoba Wax, synthetic and siliconyl jojoba wax, Hydrogenated Microcrystalline Wax, Microcrystalline Wax, synthetic, siliconyl and Hydrogenated Rice Bran Wax, Ceresin, Ozokerite, Paraffin, behenyl beeswax, synthetic, siliconyl and hydrogenated Beeswax, synthetic, hydrogenated and siliconyl Candelilla Wax, synthetic, hydrogenated and siliconyl Carnauba, wax, synthetic, hydrogenated and siliconyl lemon peel wax, synthetic, siliconyl and hydrogenated soybean wax, synthetic, siliconyl and hydrogenated sunflower wax and mixtures thereof. Preferred natural and synthetic waxes are Beeswax, Microcrystalline wax, Candellila wax, Ozokerite, and mixtures thereof.

Non-limiting examples of suitable silicone waxes include Stearyoxy trimethylsilane such as DC580 wax, $C_{30}$-$C_{45}$ alkyl methicone available as DC AMS-C30 Cosmetic Wax, stearyoxymethyl silane available as DC Silkywax 10, $C_{24}$-$C_{54}$ alkyl methicone such as DC ST-Wax 30, $C_{30}$-$C_{45}$ Alkyldimethylsilyl, Polypropyl-silsesquioxane, available as DC SW-8005 resin wax, and mixtures thereof.

Particularly preferred lipophilic structurants may be selected from fatty alcohols (such as cetyl alcohol, stearyl alcohol, or behenyl alcohol), microcrystalline waxes, stearyloxy trimethylsilane and mixtures thereof Liquid Phase A shaving aid, particularly melt-formed shaving aids with a lipophilic structurant, may further comprise from about 10% to about 70%, preferably from about 10% to about 60%, more preferably from about 10% to about 40%, by weight of the shaving aid of a liquid phase. In one aspect, the liquid phase comprises a hydrophobic material or mixtures thereof. The liquid phase may provide a number of in use benefits such as lubrication, skin feel, skin health, and cooling sensation. The liquid phase is contained within the solid shaving aid by the lipophilic structurant.

In one example, the liquid phase may have a melting point of 45° C. or less, preferably 40° C. or less, even more preferably 30° C. or less, most preferably 25° C. or less. The melting point is determined according to ASTM D5440-93. Preferably the liquid phase and the hydrophobic material is liquid at 25° C. The use of a liquid phase enables the materials such as the lipophilic structurant to be readily added and mixed upon melting thereof. In another example, the liquid phase hydrophobic material or mixtures thereof may be very slightly soluble and have a melting point of 45° C. or less, as defined herein above, and be miscible with one another. In another example, the melting point of the mixture of liquid phase and the lipophilic structurant is preferably from 45° C. to 5° C. less than the melting point of the water soluble polymer.

Suitable liquid phase components for use herein include for example natural oils, synthetic oils, silicone oils, petrolatum, triglycerides, butters or mixtures thereof. As used herein, the term "oil" includes, but is not limited to any non-aqueous substance that is very slightly soluble, preferably practically insoluble in water according to the USP definition. Petrolatum may be considered as a lipophilic structurant or a liquid phase due to its complex mixture of component materials.

The oil may be selected from natural oil, synthetic oil, silicone oil and mixtures thereof. Non-limiting examples of suitable natural oils include Acetylated Castor Oil, Acetylated Hydrogenated Castor Oil, *Actinidia chinensis* (Kiwi) Seed Oil, *Adansonia digitata* Oil, *Aleurites moluccana* Seed Oil, *Anacardium occidentale* (Cashew) Seed Oil, *Arachis hypogaea* (Peanut) Oil, *Arctium lappa* Seed Oil, *Argania spinosa* Kernel Oil, *Argemone mexicana* Oil, *Avena sativa* (Oat) Kernel Oil, *Bertholletia excelsa* Seed Oil, *Borago officinalis* Seed Oil, *Brassica campestris* (Rapeseed) Seed Oil, *Calophyllum tacamahaca* Seed Oil, *Camellia japonica* Seed Oil, *Camellia kissi* Seed Oil, *Camellia oleifera* Seed Oil, Canola Oil, Caprylic/Capric/Lauric Triglyceride, Caprylic/Capric/Linoleic Triglyceride, Caprylic/Capric/Mystic/Stearic Triglyceride, Caprylic/Capric/Stearic Triglyceride, Caprylic/Capric Triglyceride, *Carthamus tinctorius* (Hybrid Safflower) Seed Oil, *Carthamus tinctorius* (Safflower) Seed Oil, *Carum carvi* (Caraway) Seed Oil, *Carya illinoensis* (Pecan) Seed Oil, Castor Oil Benzoate, *Chenopodium quinoa* Seed Oil, *Cibotium barometz* Oil, *Citrullus vulgaris* (Watermelon) Seed Oil, *Cocos Nucifera* (Coconut) Oil, Cod Liver Oil, *Coffea arabica* (Coffee) Seed Oil, *Coix lacryma-jobi* (Job's Tears) Seed Oil, *Corylus americana* (Hazel) Seed Oil, *Corylus avellana* (Hazel) Seed Oil, *Cucumis sativus* (Cucumber) Oil, *Cucurbita pepo* (Pumpkin) Seed Oil, *Daucus carota sativa* (Carrot) Seed Oil, *Elaeis guineensis* (Palm) Kernel Oil, *Elaeis guineensis* (Palm) Oil, *Gossypium* (Cotton) Seed Oil, *Helianthus annuus* (Hybrid Sunflower) Oil, *Helianthus annuus* (Sunflower) Seed Oil, *Hippophae rhamnoides* Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, *Isatis tinctoria* Seed Oil, *Juglans regia* (Walnut) Seed Oil, Lauric/Palmitic/Oleic Triglyceride, *Umnanthes alba* (Meadowfoam) Seed Oil, *Unum usitatissimum* (Linseed) Seed Oil, *Lupinus albus* Seed Oil, *Macadamia integrifolia* Seed Oil, *Macadamia ternifolia* Seed Oil, Maleated Soybean Oil, *Mangifera indica* (Mango) Seed Oil, Marmot Oil, *Melaleuca alternifolia* (Tea Tree) Leaf Oil, *Melia azadirachta* Seed Oil, *Melissa officinalis* (Balm Mint) Seed Oil, Menhaden Oil, Mink Oil, *Moringa pterygosperma* Seed Oil, *Mortierella* Oil, Neatsfoot Oil, *Nelumbium speciosum* Flower Oil, *Nigella sativa* Seed Oil, *Oenothera biennis* (Evening Primrose) Oil, *Olea europaea* (Olive) Fruit Oil, *Olea europaea* (Olive) Husk Oil, Orange Roughy Oil, *Orbignya cohune* Seed Oil, *Orbignya oleifera* Seed Oil, *Oryza sativa* (Rice) Bran Oil, *Oryza sativa* (Rice) Germ Oil, Ostrich Oil, Oxidized Corn Oil, Oxidized Hazel Seed Oil, *Papaver orientale* (Poppy) Seed Oil, *Passiflora edulis* Seed Oil, *Persea gratissima* (Avocado) Oil, *Pistacia Vera* Seed Oil, Placental Lipids, *Prunus amygdalus amara* (Bitter Almond) Kernel Oil, *Prunus amygdalus dulcis* (Sweet Almond) Oil, *Prunus armeniaca* (Apricot) Kernel Oil, *Prunus avium* (Sweet Cherry) Seed Oil, *Prunus cerasus* (Bitter Cherry) Seed Oil, *Prunus persica* (Peach) Kernel Oil, *Pyrus malus* (Apple) Oil, *Ribes nigrum* (Black Currant) Seed Oil, *Ricinus communis* (Castor) Seed Oil, *Rosa canina* Fruit Oil, *Rosa moschata* Seed Oil, Salmon Oil, *Salvia hispanica* Seed Oil, *Santalum album* (Sandalwood) Seed Oil, *Sesamum indicum* (Sesame) Seed Oil, Shark Liver Oil, *Solanum lycopersicum* (Tomato) Seed Oil, Soybean Lipid, Sphingolipids, *Taraktogenos kurzii* Seed Oil, *Telphairia pedata* Oil, Vegetable Oil, *Vitis vinifera* (Grape) Seed Oil, *Zea mays* (Corn) Germ Oil, *Zea mays* (Corn) Oil mineral oil and mixtures thereof.

Suitable synthetic oils include hydrocarbons, esters, alkanes, alkenes and mixtures thereof. Non-limiting examples include isopropyl palmitate, isopropyl stearate, isohexadecane, isododecane, polyglyceryl triisostearate and mixtures thereof.

Non-limiting examples of suitable silicone oils include dimethicones (including partial esters of dimethicones and fatty acids derived from natural/synthetic oils), cyclomethicones, phenylated silicones, phenyl trimethicones, trimethyl pentaphenyl trisiloxane, silicone polyether block copolymers and mixtures thereof.

Suitable silicone polyether copolymers may comprise from about 1% to 50%, by weight of PEO, from about 20% to about 90% by weight of PPO, and from about 1% to about 20% by weight of silicone. Preferably, the silicone polyether copolymer comprises at least about 40%, more preferably at least about 50%, most preferably at least about 60%, by weight of PPO. In addition, the silicone polyether copolymer preferably comprises at least about 10%, more preferably from at least about 15%, most preferably from about 15% to 30% by weight of PEO. Furthermore, the silicone polyether block copolymer comprises from 1% to 20%, preferably 10% to 20%, more preferably about 15% by weight of silicone.

Whilst silicone polyether block copolymers are known in the art to provide a number of benefits such as foaming, defoaming, wetting, deaeration and lubricity, it has been found that the selection of silicone block copolymers having from 20% to 90% by weight of PPO and from 1% to 50% of PEO further provide improved lubrication whilst ensuring the required level of water dispersion and or solubility, versus silicone polyether block copolymers having less or no PPO and more PEO. Moreover, the use of such silicone block copolymers provides improved adhesion to the skin versus alternative materials such as copolymers of PEO and PPO. Furthermore, the inclusion of 1% to 20% of silicone by weight of the silicone polyether block copolymer provides desirable levels of lubrication despite being present at low levels in the polymer.

The copolymers are block copolymers and may preferably have a pendant graft structure. The silicone polyether block copolymer preferably has a ratio of PEO units to PPO units of from 3.0 to 0.1, preferably from 2.0 to 0.1, more preferably from 0.6 to 0.25. The silicone polyether block copolymer preferably has a ratio of PEO units to PPO units to silicone units of from 20:65:15.

The silicone polyether copolymer may have a molecular weight of from about 10000 to about 19000, more preferably from about 10000 to 15000. Suitable silicone polyether copolymers are available from Momentive under the SILWETS trademark products including L7210, L7602, L7220, L7230, L7500, preferably L7210 and L7602.

Non-limiting examples of commercially available silicone oils include Dow Corning 200 fluid, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.), the Viscasil series (sold by General Electric Company), SF 1075 methylphenyl fluid (sold by General Electric Company) and 556 Cosmetic Grade Fluid (sold by Dow Corning Corp.), Silshine 151 (sold by Momentive), PH1555 and PH1560 (sold by Dow Corning) and Silwets such as Silwets 7210, 7230 and 7220 (available from by Momentive).

Suitable triglycerides, may have the following formula:

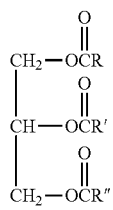

in which R, R', and R'' may be the same as, or different from, one or both of the others, and in which each of R, R', and R'' is a fatty acid and the triglyceride is solid at 25° C.

Suitable oils from which triglycerides may be formed include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion herein include Shea Butter, *Theobroma cacao* (Cocoa) Seed Butter, Cocoa Butter, *Mangifera indica* (Mango) Seed Butter, Kokum Butter and mixtures thereof. Particularly preferred are shea butter, cocoa butter and mixtures thereof.

Preferred liquid phase components may be selected from capric and or caprylic triglycerides, olive oil, shea butter, cocoa butter, petrolatum, isopropyl isostearate, dimethicones, phenylated silicones, silicone polyether block copolymers and mixtures thereof. The silicone polyether block polymers are particularly advantageous as they may facilitate the dispersion of the water soluble polymer in the lipophilic structurant as discussed hereinafter and may also improve lubrication.

Benefit Agents

According to the present disclosure, the shaving aid may optionally further comprise a hydrophobic compound or mixtures thereof. In one example, the shaving aid may comprise from 1% to 40%, preferably from 5% to 40%, more preferably from about 10% to about 40%, even preferably from about 12% to about 30% by weight of a hydrophobic compound and or mixtures thereof. Suitable hydrophobic compounds include natural oils, waxes, and/or fats; synthetic waxes or oils; triglycerides; skin active agents; sensates; fragrance oils; silicones; and mixtures thereof. The hydrophobic compound can provide a number of in use benefits such as lubrication, skin feel, skin health, and cooling sensation.

The hydrophobic compound may comprise skin active agents such as, but not limited to, oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils; peppermint oil; ISO E SUPER® [(1-(1,2,3,4,5,6,7,8-octahydro-2,3,8,8-tetramethyl-2-naphthalenyl)ethanone] (International Flavors & Fragrances Inc.); and mixtures thereof.

In some examples, the hydrophobic compound may comprise one or more sensates. Among synthetic coolants, many are derivatives of, or are structurally related to, menthol, i.e., containing the cyclohexane moiety, and derivatized with functional groups including carboxamide, ketal, ester, ether, and alcohol. Non-limiting examples include menthyl ethylamido oxalate (under the tradename FRESCOLAT® X-COOL® from Symrise), menthyl lactate (such as FRESCOLAT® ML Natural available from Symrise), and menthyl pyrrolidone carboxylate, also known as menthyl PCA (under the tradename QUESTICE® from Givaudan).

Hydrophobic compounds may be selected from capric and or caprylic triglycerides, grape seed oil, olive oil, microcrystalline wax, shea butter, cocoa butter, lanolin, essential oil, peppermint oil, isohexadecane, petrolatum, silicone polymers including waxes and oils (selected from dimethicones, phenylated silicones and mixtures thereof), and mixtures thereof.

In some examples, the shaving aid may optionally comprise any other ingredients commonly found in commercially available shaving aids. The shaving aid may therefore contain other conventional shaving aid ingredients, including water-swellable release enhancing agents such as cross-linked polyacrylics (e.g., 2% to 7% by weight), colorants, skin feel/care actives such as water soluble cationic polymers, surfactants, soaps (including interrupted soaps), antioxidants, preservatives, emollients, beard softeners, astringents, medicinal agents, plasticizers, additional lubricants, depilatories/keratolytic materials, tackifiers, skin-soothing agents, fragrances, compatibilisers, anti-inflammatory agents, antipruritic/counterirritant materials, and mixtures thereof. These ingredients may fall under the definition of hydrophobic compounds as used herein and should be included as such in determining the amount of the hydrophobic compound(s).

Compositions

TABLE 1

| Comp. No. | Composition |
|---|---|
| 1 | A composition comprising,<br>a. a lubricant; and<br>b. an antioxidant, wherein the antioxidant is represented by a general formula:<br>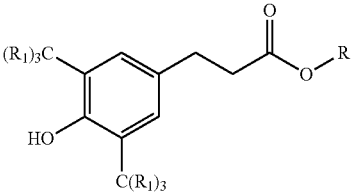<br>(I)<br>wherein R is a $C_{1-18}$ alkyl, a $C_{6-18}$ aryl, or a $C_{1-18}$ alkylaryl group; and $R_1$ is a methyl group or a hydrogen atom. |
| 2 | In one aspect of the composition 1 of Table 1, R is a methyl or an ethyl group. |
| 3 | In one aspect of compositions 1 or 2 of Table 1, the lubricant comprises at least 50% polyethylene oxide. |
| 4 | In one aspect of compositions 1-3 of Table 1, the composition further comprises a chelant. |
| 5 | In one aspect of the composition 4 of Table 1, the chelant is selected from a group consisting of citric acid and ethylenediaminetetraacetic acid. |
| 6 | In one aspect of compositions 1-5 of Table 1, the composition further comprises a matrix polymer. |
| 7 | In one aspect of the composition 6 of Table 1, the matrix polymer is ethylene vinyl acetate. |
| 8 | In one aspect of the composition 6 of Table 1, the matrix polymer has a glass-transition temperature less than 130° C. |
| 9 | In one aspect of composition 1-8 of Table 1, the antioxidant is represented by the formula:<br>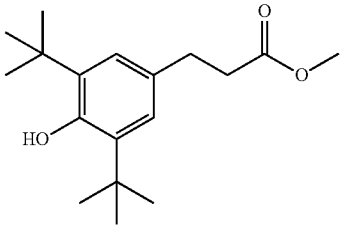<br>(II) |
| 10 | In one aspect of compositions 1-5 and 9 of Table 1, the composition further comprises a non-polymeric matrix. |
| 11 | In one aspect of the composition 10 of Table 1, the non-polymeric matrix has a melt-temperature less than 100° C. |
| 12 | In one aspect of compositions 1-11 of Table 1, the shaving aid comprises about 0.1% to about 5%, by weight of the shaving aid, of the antioxidant. |
| 13 | In one aspect of the composition 4 of Table 1, the shaving aid comprises about 0.1% to about 5%, by weight of the shaving aid, of the chelant. |

TABLE 2

| Comp. No. | Composition |
|---|---|
| 1 | A composition comprising:<br>a. a lubricant comprising a water soluble polymer; and<br>b. an antioxidant, wherein the antioxidant is represented by a general formula:<br>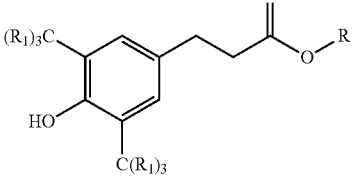<br>(I)<br>wherein R is a $C_{1-18}$ alkyl, a $C_{6-18}$ aryl, or a $C_{7-18}$ alkylaryl group; and $R_1$ is a methyl group or a hydrogen atom, wherein the water soluble polymer has an initial molecular weight of at least 1,000,000 g/mol, and wherein the water soluble polymer exhibits a molecular weight loss of less than about 500,000 g/mol within a predefined time period. |
| 2 | In one aspect of the composition 1 of Table 2, the lubricant comprises at least 50% polyethylene oxide. |
| 3 | In one aspect of composition 1 and 2 of Table 2, the composition further comprises a chelant. |
| 4 | In one aspect of the composition 3 of Table 2, the chelant is selected from a group consisting of citric acid and ethylenediaminetetraacetic acid. |
| 5 | In one aspect of compositions 1-4 of Table 2, the composition further comprises a matrix polymer. |
| 6 | In one aspect of the composition 5 of Table 2, the matrix polymer is ethylene vinyl acetate. |
| 7 | In one aspect of compositions 1-6 of Table 2, the antioxidant is represented by the formula:<br>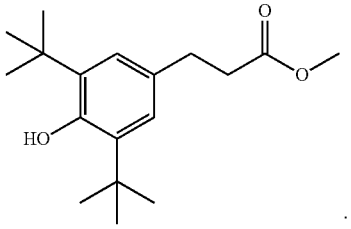 [SMILES: COC(=O)CCc1cc(C(C)(C)C)c(O)c(C(C)(C)C)c1]<br>(II) |

Methods of Manufacture/Processing

The shaving aid may be formed using any method known in the art such as molding (including melt-forming), pressing, impregnation, spray-coating, calendaring, and extrusion. All of the components of the shaving aid can be blended prior to molding or extrusion. For best results, it is preferred that the components are dry. In summary, the method comprises the steps of providing a feed comprising the lubricant, the antioxidant, the chelant, the carrier, and/or additional optional ingredients and forming the mixture by molding, pressing, impregnating, spray-coating, calendaring, and/or extruding the mixture to form a solid shaving aid. Additional optional steps may be included depending on the process of manufacture that is utilized, e.g., heating the feed to an appropriate processing temperature, mixing and shearing. The shaving aid may be formed separately from the hair removal device or formed directly onto a portion of the hair removal device, including the hair removal head.

Extrusion

The shaving aid may be extruded. Extrusion is particularly preferred where the shaving aid comprises a carrier which is a matrix polymer such as HIPS or EVA. The extrusion process generally consists of blending the components, which generally requires that the carrier be melted with heat.

The blended components may be extruded (e.g. which applies shear), such as through a HAAKE™ System 90 (Thermo Scientific) ¾ inch (~1.91 cm) diameter extruder with a barrel pressure of about 1000 psi to 2000 psi (~6.90 MPa-13.8 MPa), a rotor speed of about 10 rpm to 50 rpm, and a temperature of about 150°-185° C. and a die temperature of about 170°-185° C. Alternatively, a 1¼ inch (~3.18 cm) single screw extruder may be employed with a processing temperature of 175°-200° C., preferably 185°-190° C., a screw speed of 20 rpm to 50 rpm, preferably 25 rpm to 35 rpm, and an extrusion pressure of 1800 psi to 5000 psi (~12.4-34.5 MPa), preferably 2000 psi to 3500 psi (~13.8 MPa-24.1 MPa). The extruded shaving aid may be air cooled to about 25° C.

The shaving aid may be injection molded. To injection mold the shaving aid, the blended components may first be extruded into pellets. This can be done on a 1¼ or 1½ inch (~3.18 cm or 3.81 cm) single screw extruder at a temperature of 120° C.-180° C., preferably 140° C.-150° C., with a screw speed of 20 rpm to 100 rpm, preferably 45 rpm to 70 rpm. The pellets are then molded (with or without re-melting) in either a single material molding or multi-material molding machine, which may be single cavity or multi-cavity, and optionally equipped with a hot-runner system. The process temperature can be from 165° C. to 250° C., preferably from 180° C. to 225° C. The injection pressure should be sufficient to fill the part completely without excess flashing. Depending on the cavity size, configuration and quantity, the injection pressure can range from 300 to 2500 psi (~2.07-17.2 MPa). The cycle time is dependent on the same parameters and can range from 3 to 30 seconds, with the optimum generally being about 6 to 15 seconds.

The matrix polymer is generally heated above its glass transition temperature. The matrix polymer may be chosen to allow for lower processing temperatures. For example, the matrix polymer may be EVA and may have a glass-transition temperature less than 130° C.

The blended components may be extruded through a Rondol 18, 18 mm diameter extruder with a barrel pressure of about 500-1000 psi, a rotor speed of about 10 to 50 rpm, and a temperature of about 100°-160° C. and a die temperature of about 100°-160° C. Alternatively, a 1½ inch single screw extruder may be employed with a processing temperature of 100°-160° C., preferably 110-130° C., a screw speed of 20 to 50 rpm, preferably 25 to 50 rpm, and an extrusion pressure of 1800 to 7500 psi, preferably 4000 to 6500 psi. Other extrusion conditions can also be employed. The extruded strip is cooled to about 25° C. To injection mold the strips it is preferred to first extrude the powder blend into pellets. This can be done on a 1¼ or 1½ inch single screw extruder at a temperature of 100°-140° C., preferably 110°-130° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 100° to 185° C., preferably from 110° to 145° C. The injection pressure should be sufficient to fill the part completely without flashing. Depending on the cavity size, configuration, and quantity, the injection pressure can range from 300 to 2500 psi. The cycle time is dependent on the same parameters and can range from 3 to 30 seconds, with the optimum generally being about 6 to 15 seconds. In one embodiment, one or more feeds can be preheated or they can be fed in at ambient temperature. Methods for forming extruded shaving aids comprising EVA are further described in U.S. Pat. No. 5,349,750 and U.S. Patent Application Publication Nos. 2017/0334082 and 2018/0117780.

Melt Formed

The shaving aid may be manufactured using a melt formed process. In such processes, the ingredients are heated and stirred until melted. The molten material is then transferred into a mold, and the temperature is reduced. Optionally, pressure may be applied. The shaving aid is removed from the mold upon cooling.

The ingredients may be premixed in one fashion or another. The process may include combining a lipid phase (e.g. comprising the lipophilic structurant) and a liquid phase as previously discussed. The lipid phase and/or the liquid phase may include the lubricant, or the lubricant may be added as a separate phase.

The lipid phase may comprise a lipophilic structurant. The lipid phase may comprise from about 10% to about 70%, preferably from about 10% to 60%, more preferably from about 20% to about 40%, even more preferably from about 25% to about 35% by weight of the shaving aid of a lipophilic structurant.

Pressing

In another example, the shaving aid may be provided in the form of a tablet, bar or other solid form comprising compressed powder. For such examples, the shaving aid may be manufactured whereby the lubricant and other solid dry components are provided as particulates and mixed. The particulate material(s) is solid at 25° C. and preferably has a melting point of 30° C. or more. The shaving aid thus may comprise from 10% to 90% by weight of a particulate material(s) of the lubricant.

The shaving aid may comprise from 40% to 90% lubricant. The shaving aid may be formed by compression such as cold-compression as disclosed in US2011/0041865.

The shaving aid may comprise greater than 90% of the lubricant up to and including 100% of the lubricant (absent the preserving agent(s) of the present invention). The shaving aid may be formed by compression such as ultrasonic-compression as disclosed US2012/0023763.

The terms "compression," "compression molding," and "compression compaction" as used herein refer to a process by which the bulk density of a particulate or powder is reduced to form a solid tablet by the application of pressure. Typically, this is performed without the application of external shear force or heat. Preferably the compression compaction is conducted below the melting point of at least one, preferably all, the particulate components, preferably at an ambient temperature of 25° C. As such, the particulates retain their integrity after the compression process and are typically visible by the naked eye after the compression process is completed.

In certain examples, additional energy sources such as heat or ultrasonic energy may be applied during or after compression to increase inter-particulate bonding and increase the rigidity of the resulting shaving aid. Application of additional energy preferably does not result in any substantial melting of the particulate material. Preferably, this method does not require an extrusion or injection molding step or the application of energy sources such as heat.

The shaving aid may thus be provided in the form of a compressed solid formed from particulates. Preferably, the particulates have an average particle size distribution of from about 50 to 1250 microns and preferably from about 300 to 1250 microns, more preferably about 1000 microns. Alternatively, the particulate size is such that 90% of particles pass through a 20 mesh screen, i.e., 90% of particles are less than 841 microns in diameter. The shaving aid is compressed preferably directly into a preform or container with a compression force of typically greater than 1 KN. This may be achieved using any method and equipment known in the art such as a die press. The bulk density of the particulate material prior to compression is typically about 300 to 600 kg/m$^3$ and increases to about 1000 to 1200 kg/m$^3$ following compression. Bulk density thus may be increased by about 200% to about 400% after the compression. Without wishing to be bound by theory, it has been found that the use of particulate compression manufacturing, preferably cold particulate compression (i.e. at 25° C. or less), to form the shaving aid enables highly lubricous components to be incorporated therein without negatively impacting the water solubility and swelling performance of the water soluble polymer. This also allows flexibility in the size of the resulting shaving aid to be used for multiple razor cartridges.

Test Methods

Molecular Weight Testing

The mean molecular weight distributions were obtained using a gel permeation chromatography (GPC) system equipped with a LabFlow 4000 HPLC pump, three TSK-GEL® GMPW columns (17 µm, 300×7.5 mm) from Tosoh Corp., a TSK-GEL® PWH guard column (13 µm, 75×7.5 mm) thermostated at 35° C., and a SHIMADZU® RID-10A refractive index detector from Shimadzu Corp.

The eluent was 0.05% w/v NaN$_3$ aqueous solution provided at a flow rate of 0.8 mL/min. The concentration of the polymeric solutions was 0.2 mg/mL and the injection volume was 150 µL. Ethylene glycol (0.1 mg/mL) was added as volume marker. To obtain a PEO concentration of 0.2 mg/mL, the sample was dissolved and extracted in 25 ml of eluent for 48 hours at room temperature with an orbital stirrer at 100 rpm.

Figure 2:
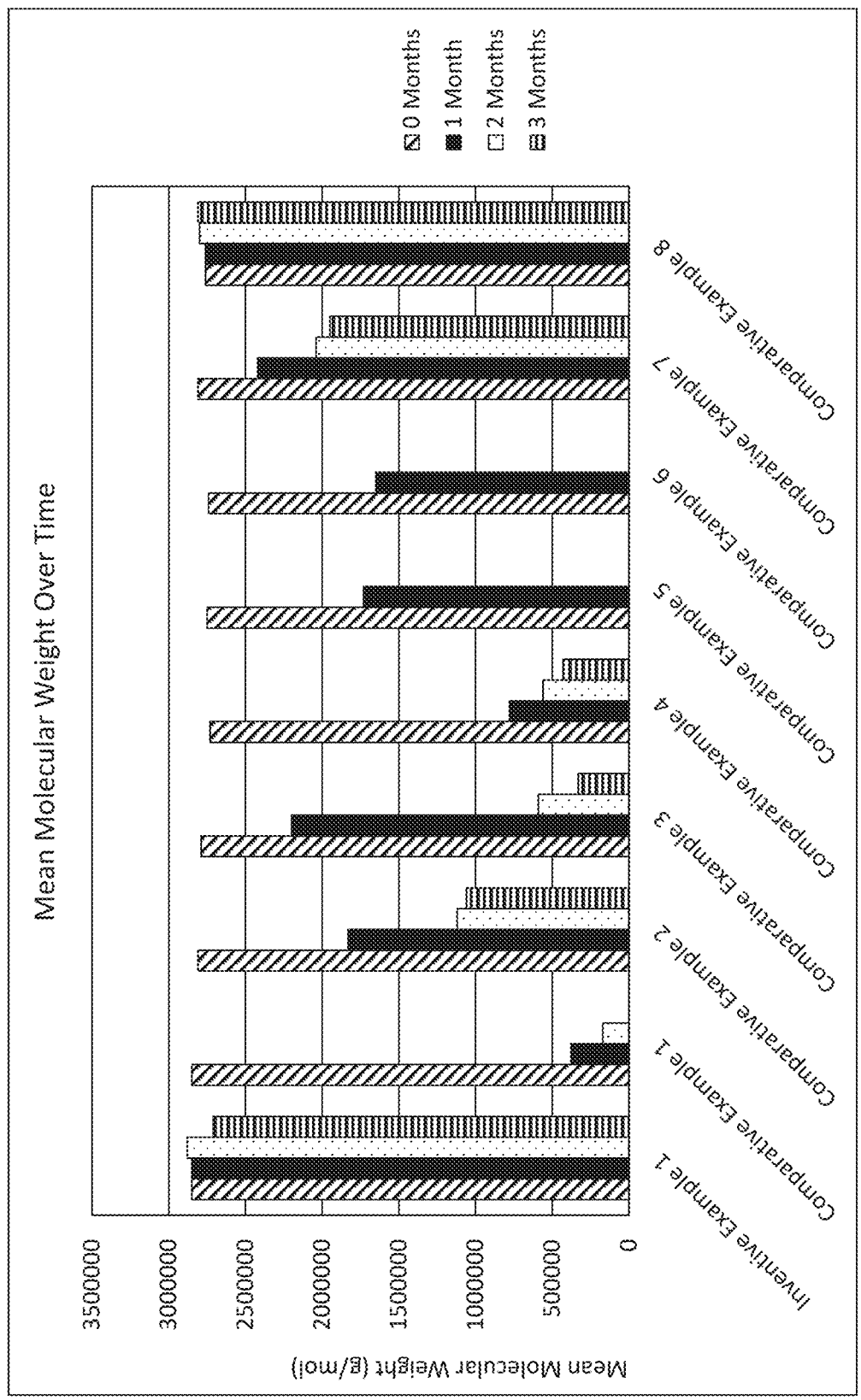
FIG. 2 is a bar graph showing the mean polyethylene oxide (PEO) molecular weight of shaving aid formulations with various antioxidants over time.

The number-average ($M_n$) and weight-average molecular weight ($M_w$) were determined by calibration with near-monodisperse PEO standards (2-885 kg/mol). Values were determined by processing the chromatograms with a Microsoft® Excel® macro (available from Microsoft Corp.) using the equations below. The data listed in this application and in FIGS. 2 and 3 represent the average of a duplicate sample preparation with duplicate injections of each preparation. Recovery was determined gravimetrically (at least two sample preparations, subtracting the percentage of leachable components from the weight of the extracted solute).

$$M_n = \frac{\sum N_i M_i}{\sum N_i}$$

$$M_w = \frac{\sum g_i M_i}{\sum g_i} = \frac{\sum N_i M_i^2}{\sum N_i M_i}$$

$$w_i = \frac{N_i M_i}{\sum N_i M_i} = \frac{g_i}{\sum g_i} = \frac{g_i}{g}$$

where $N_i$ is the number of polymeric chains; $g_i$ is the weight of polymeric chains; and $w_i$ is the weight fraction of polymeric chains with molecular weight $M_i$. $M_i$ was obtained from the elution volume by a calibration curve. $w_i$ is equal to the fraction of area of the chromatogram in an interval of ±0.025 min around the elution time corresponding to Mi.

EXAMPLES

Example 1: Example Compositions

The following example formulations of shaving aids in accordance with the present disclosure are made according to Tables 3-5 below. All values are w/w %.

The compositions listed in Table 3 are made via the corresponding extrusion process described above. For the polymer-matrix examples where EVA is the polymeric matrix, the extrusion temperature is 120° C. For examples where HIPS is the polymeric matrix, the extrusion temperature is 185° C.

TABLE 3

| Polymer-Matrix Compositions | | | | | | |
|---|---|---|---|---|---|---|
| | Ex. 1 | Ex. 2 | Ex. 3 | Ex. 4 | Ex. 5 | Ex. 6 |
| Polyox N750[1] | — | — | 21.2 | 24.4 | — | — |
| Polyox Coagulant[1] | — | — | 31.8 | 36.6 | — | — |
| Polyox 308[1] | 54.0 | 53.0 | — | — | 54.0 | 57.0 |
| EVA | 35.0 | 35.0 | 35.0 | 27.0 | 35.0 | — |
| HIPS | — | — | — | — | — | 31.0 |
| Carbowax 4600[1] | 5.0 | 5.0 | 5.0 | 5.0 | 5.0 | 5.0 |
| Polycaprolactone | 5.0 | 5.0 | 5.0 | 5.0 | 5.0 | 5.0 |
| Ralox 35[2] | 0.5 | 1.5 | 1.5 | 1.5 | 0.5 | 1.5 |
| Citric Acid | 0.5 | 0.5 | 0.5 | 0.5 | — | — |
| EDTA | — | — | — | — | 0.5 | 0.5 |

The compositions listed in Table 4 are made via the corresponding melt-formed process described above.

TABLE 4

| Melt-Formed Compositions | | | | | |
|---|---|---|---|---|---|
| | Ex. 1 | Ex. 2 | Ex. 3 | Ex. 4 | Ex. 5 |
| Behenyl Alcohol | 30.0 | 30.0 | — | — | — |
| Stearyl Alcohol | — | — | 30.0 | 30.0 | 30.0 |
| Petrolatum | 39.5 | 32.5 | 40.0 | — | 30.0 |
| Mineral Oil | — | — | — | 40.0 | — |
| PEO | 28.0 | 25.0 | 28.0 | 28.0 | 28.0 |
| Brij CS20[3] | — | 5.0 | — | — | 5.0 |
| Lauric Acid | — | 5.0 | — | — | 5.0 |
| Dowsil ES5600[1] | 0.5 | 0.5 | — | — | — |
| Ralox 35[2] | 1.5 | 1.5 | 1.5 | 1.5 | 1.5 |
| Citric Acid | 0.5 | 0.5 | 0.5 | 0.5 | 0.5 |

The compositions listed in Table 5 are made via the corresponding pressing process described above.

TABLE 5

| Pressed | | |
|---|---|---|
| | Ex. 1 | Ex. 2 |
| Cetyl alcohol | 15.0 | 5.0 |
| PEO | 57.0 | 88.5 |
| Magnesium Stearate | 2.0 | — |
| Sodium Carboxymethyl Cellulose | 25.0 | — |
| Hydroxypropylmethyl Cellulose | — | 5.0 |
| Ralox 35[2] | 0.5 | 1.0 |
| Citric Acid | 0.5 | 0.5 |

[1]Dow Chemical
[2]Raschig
[3]Croda Industrial Chemicals

Example 2: Compositions for Molecular Weight Analysis

The following example formulations of shaving aids of the present disclosure were made according to Table 6 below. All values are w/w %.

TABLE 6

|  | Inv. Ex. 1 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|---|
| Polyox 308[1] | 50.0 | 50.0 | 50.0 | 50.0 | 50.0 | 50.0 | 50.0 | 50.0 | 50.0 |
| EVA (9% VA) | 35.0 | 35.0 | 35.0 | 35.0 | 35.0 | 35.0 | 35.0 | 35.0 | 35.0 |
| Carbowax 4600[1] | 5.0 | 5.0 | 5.0 | 5.0 | 5.0 | 5.0 | 5.0 | 5.0 | 5.0 |
| PCL | 5.0 | 5.0 | 5.0 | 5.0 | 5.0 | 5.0 | 5.0 | 5.0 | 5.0 |
| Colorant | 4.0 | 4.0 | 4.0 | 4.0 | 4.0 | 4.0 | 4.0 | 4.0 | 4.0 |
| Ralox 35[2] | 0.5 | — | — | — | — | — | — | — | — |
| BHT | — | 0.5 | — | — | — | — | — | — | — |
| Citric Acid | 0.5 | 0.5 | — | 0.5 | — | — | — | — | 0.5 |
| Irganox 1010[3] | — | — | 0.5 | — | — | — | — | — | — |
| Ionol 2[4] | — | — | — | 0.5 | — | — | — | — | — |
| Vitamin E TPGS | — | — | — | — | 1 | — | — | — | — |
| Tinogard TS[3] | — | — | — | — | — | 0.5 | — | — | — |
| Vitamin E Acetate | — | — | — | — | — | — | 1.0 | — | — |
| Ionol 220[4] | — | — | — | — | — | — | — | 0.5 | — |
| PG | — | — | — | — | — | — | — | — | 0.5 |

[1]Dow Chemical
[2]Raschig
[3]BASF
[4]Oxiris

These samples were prepared in accordance with the methods described in Example 1 for the polymer-matrix compositions (e.g., Table 3).

Example 3: Molecular Weight Analysis—Compositions from Example 2

The example shaving aids prepared in accordance with Example 2 were aged for a predefined time period, up to three months in this case, at 40° C. and 75% relative humidity (RH). The samples were taken from the aging condition and tested before aging and then again at 1, 2, and 3 months to determine the weight average molecular weight of the PEO in each sample. The molecular weight was determined using the Molecular Weight Testing method described herein. The results are listed in Table 7 below and shown graphically in FIG. 2. For Comparative Examples 1, 5, and 6, a significant loss in molecular weight was observed, and testing was terminated prior to three months.

TABLE 7

| Example | Time (Months) | Weight Avg. Molecular Weight (g/mol) | Weight Reduction (g/mol) | Total Weight Reduction (g/mol) |
|---|---|---|---|---|
| Inventive Example 1 | 0 | 2,850,000 | — | 170,000 |
|  | 1 | 2,850,000 | ND* |  |
|  | 2 | 2,880,000 | ND |  |
|  | 3 | 2,710,000 | 170,000 |  |
| Comparative Example 1 | 0 | 2,850,000 | — | ** |
|  | 1 | 377,000 | 2,473,000 |  |
|  | 2 | 171,000 | 206,000 |  |
| Comparative Example 2 | 0 | 2,810,000 | — | 1,750,000 |
|  | 1 | 1,830,000 | 980,000 |  |
|  | 2 | 1,120,000 | 710,000 |  |
|  | 3 | 1,060,000 | 60,000 |  |

TABLE 7-continued

| Example | Time (Months) | Weight Avg. Molecular Weight (g/mol) | Weight Reduction (g/mol) | Total Weight Reduction (g/mol) |
|---|---|---|---|---|
| Comparative Example 3 | 0 | 2,790,000 | — | 2,460,000 |
|  | 1 | 2,200,000 | 590,000 |  |
|  | 2 | 590,000 | 1,610,000 |  |
|  | 3 | 330,000 | 260,000 |  |
| Comparative Example 4 | 0 | 2,730,000 | — | 2,300,000 |
|  | 1 | 780,000 | 1,950,000 |  |
|  | 2 | 560,000 | 220,000 |  |
|  | 3 | 430,000 | 130,000 |  |
| Comparative Example 5 | 0 | 2,750,000 | — | ** |
|  | 1 | 1,730,000 | 1,020,000 |  |
| Comparative Example 6 | 0 | 2,740,000 | — | ** |
|  | 1 | 1,650,000 | 1,090,000 |  |
| Comparative Example 7 | 0 | 2,810,000 | — | 860,000 |
|  | 1 | 2,420,000 | 390,000 |  |
|  | 2 | 2,040,000 | 380,000 |  |
|  | 3 | 1,950,000 | 90,000 |  |
| Comparative Example 8 | 0 | 2,760,000 | — | ND |
|  | 1 | 2,760,000 | ND |  |
|  | 2 | 2,800,000 | ND |  |
|  | 3 | 2,810,000 | ND |  |

*ND = not detectable
**Testing was terminated.

Inventive Example 1 containing Ralox 35 exhibited a relatively low loss in molecular weight of the PEO, specifically only about 140,000 g/mol, during the test period. While Comparative Example 8 also exhibited very low losses, the sample blackened during testing, which is undesirable. Thus, while Comparative Example 8 maintained the molecular weight of the PEO, a user would most likely replace the cartridge due to the color change, making Comparative Example 8 unsuitable for use as a shaving aid. Similarly, while Comparative Example 7 showed a relatively low molecular weight reduction during testing (860, 000), the samples began to turn yellow during testing, which is also undesirable and would make Comparative Example 7 unsuitable for use as a shaving aid.

Surprisingly, several samples containing antioxidants that share similarities in chemical structure with Ralox 35 in Inventive Example 1 had high reductions of molecular weight. Comparative Example 1 (BHT), and particularly Comparative Example 5 (Tinogard TS), exhibited a significant loss in molecular weight prior to three months.

Example 4: Molecular Weight Analysis—Different Chelants or No Antioxidant

The example shaving aids of Table 8 were prepared in accordance with the method described in Example 1 for the polymer-matrix compositions (e.g., Table 3) and aged in accordance with Example 3. All values in Table 8 are w/w %. The results of the molecular weight analysis of the example shaving aids of Table 8 are listed in Table 9 below and shown graphically in FIGS. 3A and 3B.

TABLE 8

|  | 0.5% Ralox 35/ 0.5% Citric acid | 0.5% Ralox 35 | 0.5% Citric Acid | 0.5% Ralox 35/ 0.5% Citric Acid |
| --- | --- | --- | --- | --- |
| Polyox 308[1] | 51.0 | 51.5 | 51.5 | 51.0 |
| EVA | 35.0 | 35.0 | 35.0 | 35.0 |
| Carbowax 4600[1] | 5.0 | 5.0 | 5.0 | 5.0 |
| Polycaprolactone | 4.0 | 4.0 | 4.0 | 4.0 |
| Colorant | 4.0 | 4.0 | 4.0 | 4.0 |
| Ralox 35[2] | 0.5 | 0.5 | — | 0.5 |
| Citric Acid | 0.5 | 0.5 | 0.5 | — |
| EDTA | — | — | — | 0.5 |

[1]Dow Chemical
[2]Raschig

TABLE 9

| Example | Weight Avg. Molecular Weight (g/mol) at 0 Months | Weight Avg. Molecular Weight (g/mol) at 3 Months | Weight Reduction (g/mol) |
| --- | --- | --- | --- |
| 0.5% Citric Acid | 2,700,000 | 210,000 | 2,490,000 |
| 0.5% Ralox 35/ 0.5% Citric Acid | 2,780,000 | 2,670,000 | 110,000 |
| 0.5% Ralox 35/ 0.5% EDTA | 2,760,000 | 2,590,000 | 170,000 |
| 0.5% Ralox 35 | 2,710,000 | 2,500,000 | 210,000 |

Figure 3A:
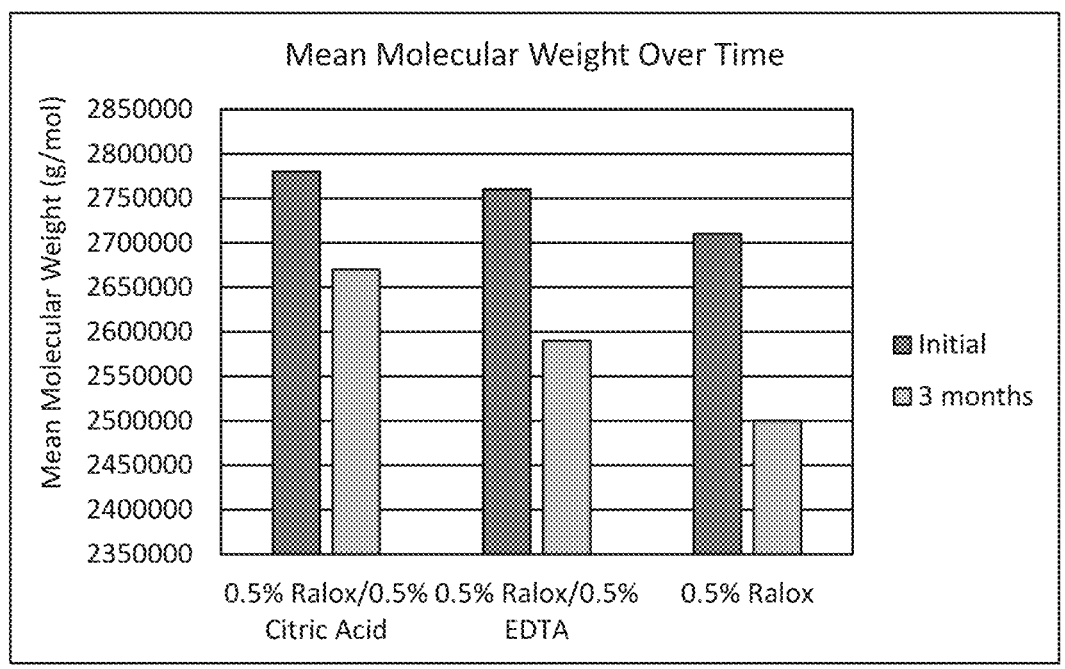
FIG. 3A is a bar graph showing the mean PEO molecular weight of shaving aid formulations with various antioxidant/chelant combinations over time.
Figure 3B:
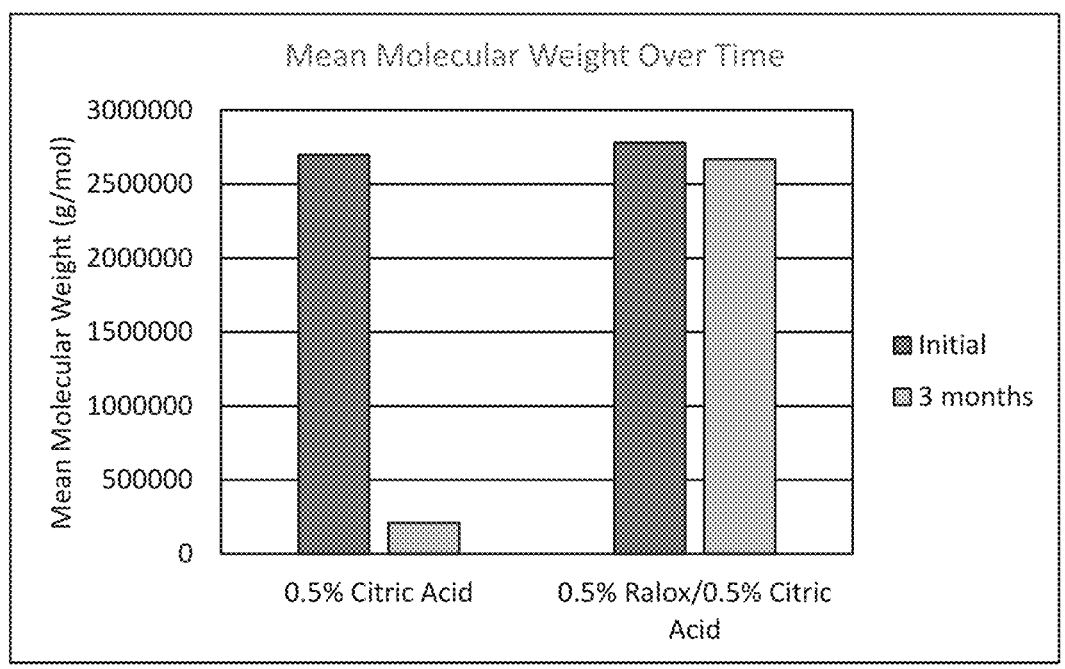
FIG. 3B is a bar graph showing the mean PEO molecular weight of shaving aid formulations with and without an antioxidant over time.

As shown in FIG. 3A, the example compositions containing an antioxidant (Ralox 35) and a chelant (citric acid or EDTA) both exhibited a relatively low loss in molecular weight of the PEO. The example composition in FIG. 3A containing only Ralox 35 still exhibited a relatively low loss in molecular weight of the PEO but the loss was higher when compared to the compositions containing Ralox 35 with a chelant. As shown in FIG. 3B, the example composition having only citric acid showed a significantly higher loss in the molecular weight of the PEO, as compared to the example with Ralox 35.

Example 5: Preparation of Samples for Descriptive Analysis

The following example formulations of shaving aids were made according to Table 10 below. All values are w/w %.

TABLE 10

|  | Inventive Example | Current Example | Control |
| --- | --- | --- | --- |
| Polyox N750[1] | 22.8 | 23.2 | 44.35 |
| Polyox 308 | 34.2 | 34.8 | — |
| Polyox Coagulant | — | — | 17.9 |
| EVA (9% VA) | 31.0 | 31.0 | — |
| HIPS | — | — | 27.5 |
| Carbowax 4600[1] | 5.0 | 5.0 | 5.0 |
| PCL | 5.0 | 5.0 | 5.0 |
| Ralox 35[2] | 1.5 | — | — |
| Citric Acid | 0.5 | — | — |
| Irganox 1010[3] | — | 1.0 | — |
| Irganox B215[3] | — | — | 0.25 |

[1]Dow Chemical
[2]Raschig
[3]BASF

All examples were prepared in accordance with the methods described in Example 1 for the polymer-matrix compositions (e.g., Table 3).

Example 6: Molecular Weight Analysis of Samples for Descriptive Analysis

Figure 4:
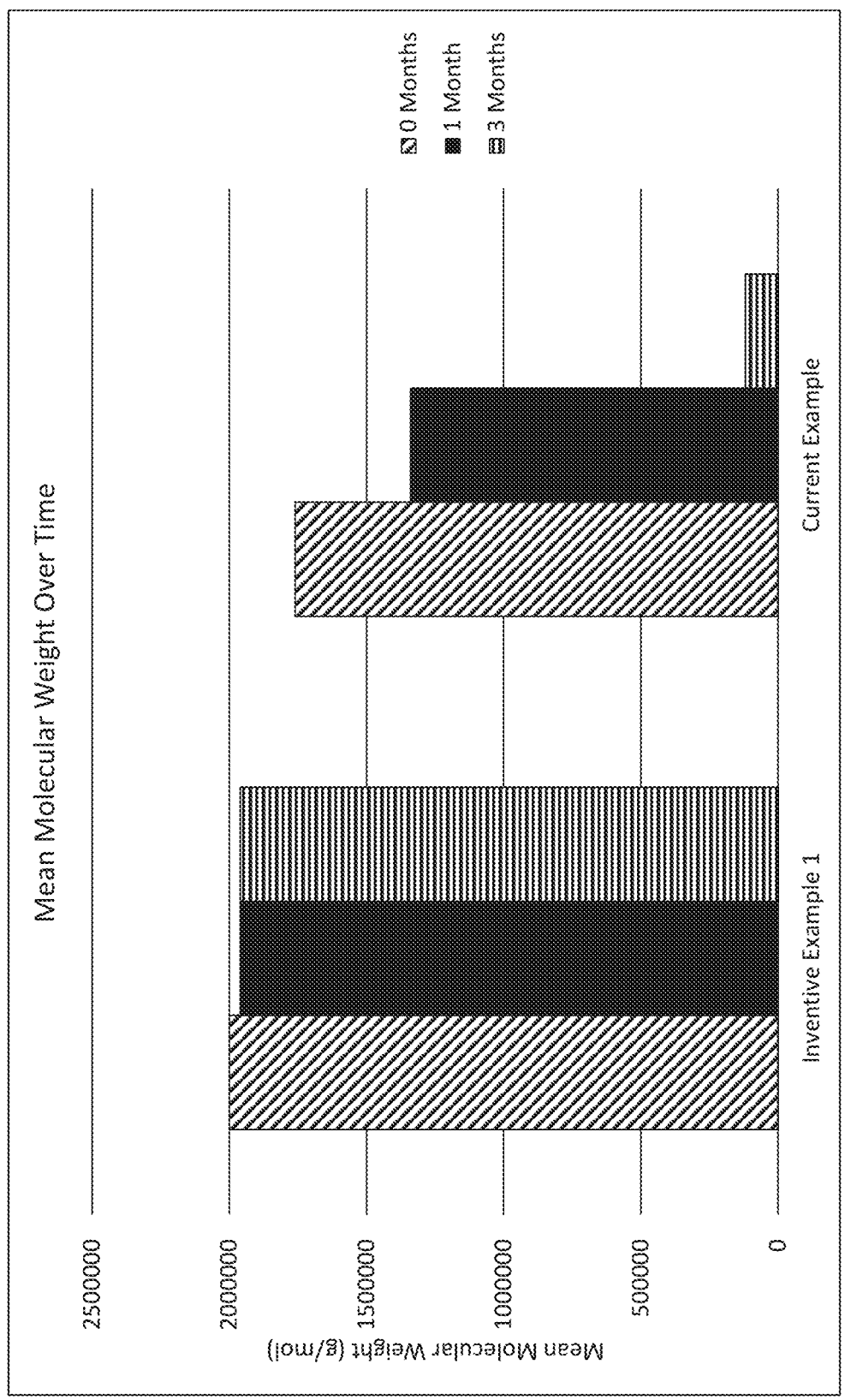
FIG. 4 is a bar graph showing the mean PEO molecular weight of the shaving aid formulations used for the Descriptive Analysis Panel over time.

The Inventive and Current Example shaving aids from Table 10 were aged for up to 3 months at 40° C. and 75% RH with samples taken and measured prior to testing and at 1 month and 3 months. The weight average molecular weight of the PEO was determined for each of the shaving aids using the Molecular Weight Testing Method described above. The results are listed in Table 11 below and shown graphically in FIG. 4. The Control was stored under ambient conditions prior to testing and the molecular weight of the PEO was not analyzed for the Control.

TABLE 11

| Example | Time (Months) | Mean Molecular Weight (g/mol) | Weight Reduction per Month (g/mol) | Total Weight Reduction (g/mol) |
| --- | --- | --- | --- | --- |
| Inventive Example | 0 | 2,000,000 | — | 40,000 |
|  | 1 | 1,960,000 | 40,000 |  |
|  | 3 | 1,960,000 | ND |  |
| Current Example | 0 | 1,760,000 | — | 570,000 |
|  | 1 | 1,340,000 | 420,000 |  |
|  | 3 | 1,190,000 | 150,000 |  |

Example 7: Descriptive Analysis Panel

As discussed above, maintaining the molecular weight of the water soluble polymer, e.g., PEO, lowers the CoF of the viscoelastic fluid formed when the water soluble polymer partially dissolves in water, which generally leads to a more pleasant shaving experience for the user. Various environmental factors can reduce the stability of the water soluble polymer, such as high temperatures or exposure to water and/or oxygen, all of which are fairly common during shaving. Eventually, the molecular weight of the water soluble polymer will be reduced beyond a user's acceptable comfort limits and cause the user to replace the razor cartridge. This threshold reduction level has been set to 500,000 g/mol based on data from the Descriptive Analysis Panel described herein. The predefined time period of aging may be set to any desired amount of time, but 3 months was selected due to the use of this time period in international stability standards for cosmetics.

Testing was conducted using a panel of trained shavers. Throughout testing, the shavers used razors containing a control shaving aid (Control), a shaving aid currently being sold (Current Example), or a shaving aid in accordance with the present disclosure (Inventive Example), as set out in Table 10 above. The average scores for the Current Example and the Inventive Example were compared to the average score for the Control.

Table 12 below shows how the average score for the Current Example and the Inventive Example differed from the Control. A negative number would indicate that the example performed worse than the Control, a positive number indicates that the example performed better than the Control, and a zero indicates that there was no noticeable difference in performance between the Example and the Control.

TABLE 12

| Example | Razor Glide | Scraping | Tug and Pull |
|---|---|---|---|
| Current Example | 0.0 | 0.0 | 0.0 |
| Inventive Example 2 | 1.2 | 0.6 | 0.4 |

The data in Table 12 indicates that the razor with the Inventive Example shaving aid demonstrated measurable improvements, including improved razor glide and decreased scraping and tug and pull.

The illustrations presented herein are not intended to be actual views of any particular substrate, apparatus (e.g., device, system, etc.), or method, but are merely idealized and/or schematic representations that are employed to describe and illustrate various examples of the disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shaving aid, comprising:
   a. a lubricant; and
   b. an antioxidant, wherein the antioxidant is represented by a general formula:

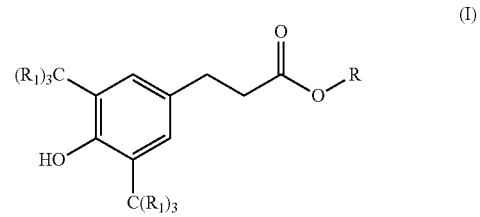

wherein R is a methyl or an ethyl group; and $R_1$ is a methyl group or a hydrogen atom.

2. The shaving aid of claim 1, wherein the lubricant comprises at least 50% polyethylene oxide.

3. The shaving aid of claim 1, further comprising a chelant.

4. The shaving aid of claim 3, wherein the chelant is selected from a group consisting of citric acid and ethylenediaminetetraacetic acid.

5. The shaving aid of claim 1, further comprising a matrix polymer.

6. The shaving aid of claim 5, wherein the matrix polymer is ethylene vinyl acetate.

7. The shaving aid of claim 5, wherein the matrix polymer has a glass-transition temperature less than 130° C.

8. The shaving aid of claim 1, wherein the antioxidant is represented by a formula:

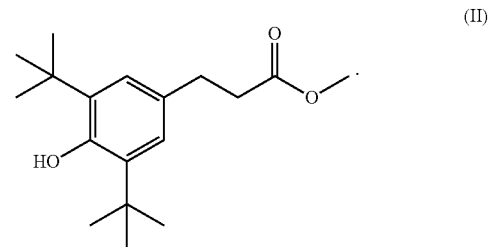 [SMILES: COC(=O)CCc1cc(C(C)(C)C)c(O)c(C(C)(C)C)c1]

9. The shaving aid of claim 1, further comprising a non-polymeric matrix.

10. The shaving aid of claim 9, wherein the non-polymeric matrix has a melt-temperature less than 100° C.

11. The shaving aid of claim 1, wherein the shaving aid comprises about 0.1% to about 5%, by weight of the shaving aid, of the antioxidant.

12. The shaving aid of claim 3, wherein the shaving aid comprises about 0.1% to about 5%, by weight of the shaving aid, of the chelant.

13. A shaving aid, comprising:
   a. a lubricant comprising a water soluble polymer; and
   b. an antioxidant, wherein the antioxidant is represented by a general formula:

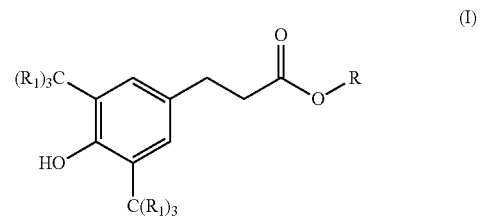

wherein R is a $C_{1-18}$ alkyl, a $C_{6-18}$ aryl, or a $C_{7-18}$ alkylaryl group; and $R_1$ is a methyl group or a hydrogen atom, wherein the water soluble polymer has an initial molecular weight of at least 1,000,000 g/mol, and wherein the water soluble polymer exhibits a molecular weight loss of less than about 500,000 g/mol within a predefined time period.

14. The shaving aid of claim 13, wherein the lubricant comprises at least 50% polyethylene oxide.

15. The shaving aid of claim 13, further comprising a chelant.

16. The shaving aid of claim 15, wherein the chelant is selected from a group consisting of citric acid and ethylenediaminetetraacetic acid.

17. The shaving aid of claim 13, further comprising a matrix polymer.

18. The shaving aid of claim 17, wherein the matrix polymer is ethylene vinyl acetate.

19. The shaving aid of claim 13, wherein the antioxidant is represented by a formula:

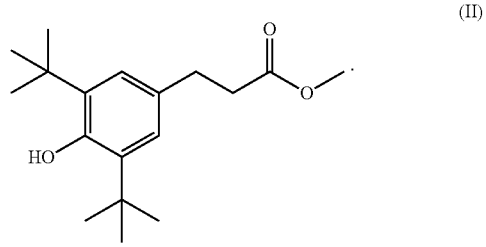 [SMILES: COC(=O)CCc1cc(C(C)(C)C)c(O)c(C(C)(C)C)c1]

(II)

* * * * *